United States Patent [19]

Yanagihara et al.

[11] Patent Number: 5,078,931
[45] Date of Patent: Jan. 7, 1992

[54] GAS-PERMEABLE, WATERPROOF FILM AND PROCESS FOR ITS PRODUCTION

[75] Inventors: Takeshi Yanagihara; Tsugio Honda; Makoto Nakano; Hiroshi Kajino, all of Kanagawa, Japan

[73] Assignee: Mitsui Toatsu Chemicals, Inc., Tokyo, Japan

[21] Appl. No.: 531,080

[22] Filed: May 31, 1990

Related U.S. Application Data

[63] Continuation-in-part of Ser. No. 233,655, Jul. 15, 1988, abandoned.

[30] Foreign Application Priority Data

Nov. 17, 1986 [JP] Japan .................. 61-274590

[51] Int. Cl.$^5$ .................................. B29C 43/24
[52] U.S. Cl. ......................... 264/41; 264/46.3; 264/175; 264/DIG. 62
[58] Field of Search ........... 264/175, 46.3, DIG. 62, 264/41, 211

[56] References Cited

U.S. PATENT DOCUMENTS

| | | | |
|---|---|---|---|
| 2,618,580 | 11/1952 | Lancaster | 264/175 |
| 3,401,129 | 9/1968 | McGinley | 264/175 |
| 3,499,957 | 3/1970 | Ancker | 264/175 |
| 3,660,551 | 5/1972 | Susuki et al. | 264/175 |
| 3,903,234 | 9/1975 | Ikeda et al. | 264/DIG. 62 |
| 3,992,496 | 11/1976 | Matsunaga et al. | 264/175 |
| 3,994,845 | 11/1976 | Blachford | 264/175 |
| 4,031,041 | 6/1977 | Bouy et al. | 364/175 |
| 4,116,892 | 9/1978 | Schwanz | 264/49 |
| 4,120,931 | 10/1978 | Fukushima et al. | 264/175 |
| 4,148,780 | 4/1979 | Blümel et al. | 264/175 |
| 4,153,661 | 5/1979 | Ree et al. | 264/175 |
| 4,306,927 | 12/1981 | Funk et al. | 264/175 |
| 4,311,658 | 1/1982 | Nicoll | 264/175 |
| 4,345,046 | 8/1982 | Ejk et al. | 264/175 |
| 4,385,139 | 5/1983 | Küchler et al. | 264/175 |
| 4,615,853 | 10/1986 | Aogama et al. | 264/175 |
| 4,704,238 | 11/1987 | Okuyama et al. | 264/211 |
| 4,705,812 | 11/1987 | Ito et al. | 264/41 |
| 4,705,813 | 11/1987 | Ito et al. | 264/41 |

FOREIGN PATENT DOCUMENTS

| | | |
|---|---|---|
| 1096117 | 2/1981 | Canada . |
| 2641533 | 3/1977 | Fed. Rep. of Germany . |
| 56-26076 | 3/1981 | Japan . |
| 0844801 | 8/1960 | United Kingdom ....... 264/46.1 |
| 1521579 | 8/1978 | United Kingdom . |

*Primary Examiner*—Hubert C. Lorin
*Attorney, Agent, or Firm*—Kane, Dalsimer, Sullivan, Kurucz, Levy, Eisele and Richard

[57] ABSTRACT

A porous waterproof film having a superior gas-permeability and waterproofness, capable of being produced under simple processing conditions, by means of simple processing equipments and at cheap cost, having superior mechanical strengths and also suitable for disposable use applications and a process for producing the film are provided, which film is obtained by subjecting a thermoplastic resin composition film comprising a thermoplastic resin and a specified quantity of a filler based on the thermoplastic resin to calender processing.

2 Claims, 1 Drawing Sheet

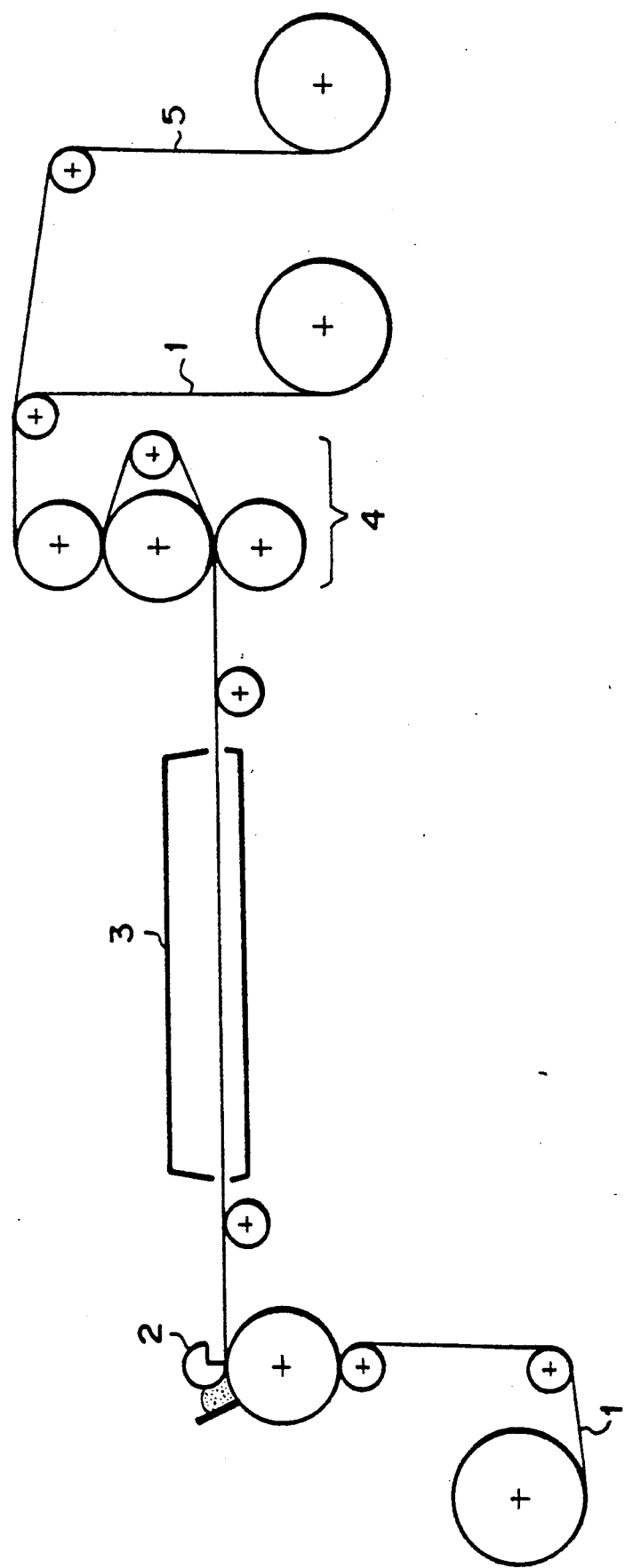

GAS-PERMEABLE, WATERPROOF FILM AND PROCESS FOR ITS PRODUCTION

CROSS REFERENCE TO RELATED APPLICATION

This application is a continuation-in-part of our copending U.S. Patent Application Ser. No. 233,655 filed July 15, 1988, now abandoned.

BACKGROUND OF THE INVENTION

1. Field of the Invention

This invention relates to a porous waterproof film having both of gas-permeability and waterproofness and a process for producing the same.

2. Brief Description of the Prior Art

The prior art directed to porous waterproof film has mostly been carried out mainly by subjecting a gas-permeable film substrate to a coating process with a resin to form a resin film on the substrate and thereby impart a superior waterproofness thereto. However, according to such a process, it has been difficult to impart a sufficient gas-permeability and the resulting product has been difficult to be regarded as a substantially gas-permeable waterproof film, and further, dampness due to sweat and moisture excreted from the body at the time of its wearing has given a disagreeable feeling.

As a technique for solving this problem, a process referred to as wet coating process has been known. For example, Japanese patent application laid-open No. Sho 56-26076 discloses a process wherein a solution of an urethane polymer dissolved in a polar organic solvent is coated onto a substrate, followed by dripping the resulting material in a water bath to remove the polar solvent and thereby form a finely porous polyurethane film having a gas-permeability. However, the process has drawbacks that the production steps are complicated and the allowable ranges of the production conditions are narrow.

According to the process, since a polyurethane resin which is an expensive raw material is used and particular processing conditions and processing equipments are required, the resulting film is so expensive that the resulting product can be used only for limited high-class clothes; hence the product has a drawback that it cannot be used for example for disposable uses or similar uses.

An object of the present invention is to provide a porous waterproof film which is superior in both of the properties of gas-permeability and waterproofness.

Another object of the present invention is to provide a porous waterproof film which can be produced under simple processing conditions and using simple processing equipments.

Still another object of the present invention is to provide a porous waterproof film which can be produced at cheap cost and hence is suitable to disposable uses.

Further still another object of the present invention is to provide a porous waterproof film having superior mechanical strengths.

Still another object of the present invention is to provide a process for producing a porous waterproof film having the above-mentioned properties.

SUMMARY OF THE INVENTION

In accordance with the present invention, there are provided a gas-permeable waterproof film which comprises 100 parts by weight of a thermoplastic resin and 1 to 50 parts by weight of a thermoplastic or thermosetting organic resin filler and having fine pores formed by calender processing; and a process for producing a gas-permeable waterproof film which comprises subjecting to calender processing, a thermoplastic resin composition film comprising 100 parts by weight of a thermoplastic resin and 1 to 50 parts by weight of a thermoplastic or thermosetting organic resin filler.

BRIEF DESCRIPTION OF THE DRAWING

The accompanying drawing is a schematic showing the steps in the process of the invention as carried out in the Example 1.

DETAILED DESCRIPTION OF THE PREFERRED EMBODIMENTS

As the thermoplastic resin used in the present invention, those which match the film in the aspect of its strengths, waterproofness, feeling, appearance, cost, etc. are used.

Concrete examples thereof are acrylic resins, urethane resins, synthetic rubbers, ethylene-vinyl acetate copolymer resins, etc.

Examples of acrylic resins are polymers of alkyl acrylates or alkyl methacrylates such as methyl acrylate, methyl methacrylate, ethyl acrylate, ethyl methacrylate, propyl acrylate, propyl methacrylate, butyl acrylate, butyl methacrylate, pentyl acrylate, pentyl methacrylate, hexyl acrylate, hexyl methacrylate, heptyl acrylate, heptyl methacrylate, octyl acrylate, octyl methacrylate, octadecyl acrylate, octadecyl methacrylate, etc. and copolymers of the foregoing esters with ethylenic unsaturated aromatic monomers such as styrene, α-methylstyrene, vinyltoluene, etc., unsaturated nitriles such as acrylonitrile, methacrylonitrile, etc., vinyl esters such as vinyl acetate and vinyl propionate, ethylenic unsaturated carboxylic acids such as acrylic acid, methacrylic acid, itaconic acid, fumaric acid, maleic anhydride, crotonic acid, etc., hydroxyalkyl ethylenic unsaturated carboxylates such as 2-hydroxypropyl acrylate, 2-hydroxyethyl methacrylate, etc., glycidyl ethylenic unsaturated carboxylates such as glycidyl acrylate, glycidyl methacrylate, etc., and acrylamide, methacrylamide, N-methylol acrylamide, N-methylol methacrylamide, N-butoxymethyl acrylamide, diacetone acrylamide, etc.

Examples of urethane resins are polyester or polyether urethane elastomers prepared from polyesters or polyether diols and diisocyanates.

Polyesters referred to herein are those obtained by polycondensation of polycarboxylic acids with polyols.

Examples of the polycarboxylic acids referred to herein are aliphatic saturated dibasic acids such as malonic acid, succinic acid, glutanic acid, adipic acid, azelaic acid, sebacic acid, hexahydrophthalic anhydride, etc., aliphatic unsaturated dibasic acids such as maleic acid, maleic anhydride, fumaric acid, itaconic acid, citraconic acid, etc., aromatic dibasic acids such as phthalic anhydride, phthalic acid, terephthalic acid, isophthalic acid, etc., and lower alkyl esters of the foregoing.

Examples of the polyols referred to herein are diols such as ethylene glycol, 1,2-propylene glycol, 1,3-propylene glycol, 1,3-butylene glycol, 1,4-butylene glycol, 1,6-hexanediol, neopentyl glycol, diethylene glycol, dipropylene glycol, hydrogenated disphenol A, adduct of bisphenol A to ethylene oxide, adduct of bisphenol A to propylene oxide, etc., and triols such as glycerine, trimethylolpropane, trimethylolethane, etc.

Examples of polyether diols are polyethylene glycol, polypropylene glycol, polytetramethylene glycol, polycaprolactone, etc., and these may also be used as polyols which are used in the preparation of polyesters.

Examples of diisocyanates to be reacted with the above polyesters or polyether diols are hexamethylene diisocyanate, isophorone diisocyanate, tolylene diisocyanate, diphenylmethane diisocyanate, xylene diisocyanate, tetramethylxylene diisocyanate, etc.

As the synthetic rubbers, copolymers of at least one of styrene, methyl methacrylate and acrylonitrile with butadiene may be used. If necessary, copolymers of the foregoing with a functional group monomer such as ethylenic unsaturated carboxylic acids such as acrylic acid, methacrylic acid, itaconic acid, fumaric acid, maleic anhydride, crotonic acid, etc., hydroxyalkyl ethylenic unsaturated carboxylates such as 2-hydroxypropyl acrylate, 2-hydroxyethyl methacrylate, etc., glycidyl ethylenic unsaturated carboxylates such as glycydyl acrylate, glycidyl methacrylate, etc. and acrylamide, methacryl amide, N-methylol acrylamide, N-methylol methacrylamide, N-butoxymethyl acrylamide, diacetone acrylamide, etc.

The filler used in the present invention refers to fine organic particles of a thermoplastic or thermosetting resin. The form thereof is not always necessary to be spherical, but it may be hollow, flat, acicular or porous, that is, it has no particular limitation. Examples thereof are fine particles of fluorine resins, silicone resins, polyethylene, polypropylene, ethylene-vinyl acetate resins, nylon, polyester resins, polyamide resins, polystyrene resin, acrylic resins, cellulose acetate, butyrate resins, urea resins, phenolic resins, epoxy resins, etc. Concrete examples of such fillers are U PEARL (urea resin; trademark of a product made by Mitsui Toatsu Chemicals, Inc.), BARINAX (polyester resin; trademark of a product made by Mitsui Toatsu Chemicals, Inc.), KPL (fluorine resin; trademark of a product made by Kitamura Company), FLO-THENE (polyethylene resin; trademark of a product made by Seitetsu Kagaku Company), etc. The resins are not limited particularly to the above resins as far as fine particles can be made therefrom. The above fillers may be used alone or in adequate admixture.

In view of waterproofness, the filler itself is preferred to be water-repellent, and fluorine resins, silicone resins, polyethylene, polypropylene, etc. are more suitable.

The particular size of the filler is in the range of 1 to 50 $\mu m$, more preferably 3 to 40 $\mu m$ in terms of the average particle size. Further, it is preferred to have the same thickness as or larger than that of the resulting porous waterproofing film. The average particle size referred to herein means the size of a secondary particle regarded as one particle in the case where particles agglomerate. Further, as to the particle size, when the filler particle is spherical, it refers to the diameter of the spherical particle, while when the particle is non-spherical, it refers to a diameter calculated from that of a spherical body having the same volume as that of the non-spherical particle.

The quantity of the filler used in the present invention is in the range of 1 to 50 parts by weight, preferably 5 to 30 parts by weight based on 100 parts by weight of the termoplastic resin. If the quantity is less than 1 part by weight, no sufficient air permeability is obtained, while if it exceeds 50 parts by weight, it is difficult to retain the strength as the film and also the resulting product is inferior in the waterproofness.

The porous waterproof film of the present invention may be a film composed only of a thermoplastic resin composition, but it may also be a composite film composed of the above-mentioned film and another porous film. Such a composite porous waterproof film may be those obtained by arranging another porous film on the one surface of thermoplastic resin composition film, or those obtained by arranging two thermoplastic composition films on both the surfaces of another porous film in a sandwich form. Further, the above-mentioned another film may be a film of a single kind, but it may also be those obtained by integrating films of the same or different kinds in a conventional manner. For example, a film of a sandwich type obtained by arranging a hydrophilic film on the one surface of a thermoplastic resin composition film and a hydrophobic film on the other surface thereof is suitable for clothing use applications. Thus, the porous waterproof film of the present invention is possible to vary depending on the uses; hence it has no particular limitation.

The above-mentioned another film has no particular limitation as far as it is of itself in a porous sheet or a film form. For example, clothes, paper, etc. may be mentioned. The paper may include a water-absorbing paper of 100% pulp, a sized paper obtained by subjecting pulp to sizing treatment, a paper made from pulp and rayon in admixture, Japanese paper, etc. It is preferred to use a paper of long fiber pulp composed of pulp fibers having relatively large clearances between one another and hence a superior gas-permeability and also having a good feeling. The clothes may include those of synthetic fibers such as polyester, nylon, acrylic fibers, natural fibers such as cotton, wool, etc., combined fibers of synthetic fibers with natural fibers, etc., and suitable ones are chosen from among the above, depending on their use applications, but it is preferred to use those having a feeling as good as possible.

The thickness of the porous waterproof film is suitably chosen depending on its use object, etc., but usually it is in the range of 1 to 50 $\mu$. In addition, in the case of a composite porous waterproof film, the basis weight of the above another film has no particular limitation, but it is preferred to be in the range of 10 to 120 $g/m^2$, and the thickness of the thermoplastic resin sheet is in the range of 1 to 50$\mu$.

As the process for producing the porous waterproof film, the following may be illustrated:

First in the case of the thermoplastic resin composition film, alone, its representative example is a process of making a film from a mixture of a thermoplastic resin with a filler, followed by subjecting it to calender processing. In this case, the process for forming the film has no particular limitation, but it is necessary to choose an adequate film-making process depending on the specific features of thermoplastic resins used. For example, in the case of acrylic resins, urethane resins, synthetic rubbers, etc., it has often been commercially employed to form a film in the form of solvent solutions of these resins or aqueous dispersions e.g. latex, emulsion, etc. thereof according to coating process. At that time, in order to improve the strength of the thermoplastic resin film and improve the waterproofness of the film, a curing agent may be contained therein. Particularly in the case of the solvent solutions or aqueous dispersions, if the thermoplastic resins have a functional group, a curing agent may often be used at the same time. As such a curing agent, melamine resins, urea resins, epoxy resins, metal chelate compounds, isocyanate compounds, aziridine compounds, etc. may be used if necessary.

In the case of coating process, for example, the solvent solution or aqueous emulsion of the thermoplastic resin may be applied directly onto a release paper or a release film by means of a coater such as knife coater, bar coater, roll coater, flow coater or the like, followed by drying the resulting material to form a film and then stripping the resulting film from the release paper or the release film to obtain the film.

The filler is necessary to choose also taking into account the above production process of the waterproof film. For example, in the case where it is produced using a solvent solution, it is necessary to choose a filler insoluble in the solvent used. In the case where it is produced using an aqueous dispersion, it is necessary to choose a filler which is unchanged in the properties by water. As described above, an adequate filler varies depending on the state employed.

Imparting of the gas-permeability is carried out by subjecting the thus-obtained resin composition films or composite films to calender processing. Namely, an external force is applied onto a thermoplastic resin composition film having a filler mixed with and dispersed in a thermoplastic resin according to calender processing to form clearances between the filler and the thermoplastic resin film and also break the surface of the continued film, whereby continued fine pores are prepared to obtain the gas-permeability.

As to the gas-permeability, usually the higher the linear pressure of calender and the larger the number of times of calendering, the easier the imparting of the gas-permeability. Thus, the control of the gas-permeability required may be easily effected by choosing the film thickness, the kind, average particle diameter and added quantity of the filler, calender conditions, etc. Usually, the calender temperature is preferably in the range of 0° to 150° C., more preferably 15° to 100° C. and the linear pressure is preferably in the range of 1 to 200 kg/cm, more preferably 10 to 100 kg/cm. The calender velocity is preferably in the range of 5 to 200 m/min., more preferably 10 to 100 m/min. Further, the number of times of the calendering has no particular limitation, but usually it is in the range of once to 10 times.

Next, as the process for producing a composite porous waterproof film, its representative examples are as follows:

According to a first process, a film composed only of a thermoplastic resin composition containing a filler is formed according to the above-mentioned process, followed by subjecting the film to calender processing to impart gas-permeability to the film and then applying the resulting film onto another film. According to a second process, a film composed of a thermoplastic resin composition containing a filler is formed, followed by applying to film onto another film and then subjecting the resulting material to calender processing to impart gas-permeability. According to a third process, a thermoplastic resin composition containing a filler is coated directly onto another film, followed by subjecting the resulting film to calender processing to impart air permeability. In the aspect of processing steps, the third process which requires no adhesion step is preferred, but even the second process has an advantage that the calender processing and the adhesion step can be carried out at the same time, depending on the choice of the thermoplastic resins. Further, the first and second processes are effective particularly in the case where the another film has a low basis weight and hence wide meshes so that even when it is directly coated, no uniform film is obtained.

As to the process for forming the film according to the first and second processes, it is necessary to choose an adequate film-forming process depending on the specific features of the thermoplastic resins employed, as in the above-mentioned case of the porous waterproof film composed only of a thermoplastic resin composition, and the choice of thermoplastic resins is also likewise made.

In the third process wherein a thermoplastic resin composition film is coated directly onto another film, the coating may be carried out in the same manner as in the case of the above-mentioned porous waterproof film composed only of a thermoplastic resin composition. Simultaneous use of a curing agnet is the same as the above.

Further, in any of the above processes, the choice of a filler is carried out in the same manner as in the case of the porous waterproof film composed only of a thermoplastic resin composition. The conditions of calender processing, etc. are also the same as in the case of the porous waterproof film composed only of a thermoplastic resin composition.

The surface of the thus formed porous waterproof film (a thermoplastic resin composition film in the case of the composit film) is practically preferred to have an gas-permeable hole diameter of 0.1 to 10 μm, more preferably 0.5 to 5 μm since the gas-permeability and the waterproofness are well balanced within such a range.

The control of the diameter of the gas-permeable holes may be carried out by adequately choosing the film thickness, the kind, average particle diameter and added quantity of the filler, calender conditions, etc. as described above.

Further, in order to improve the waterproofness and water-repellency, water-repelling treatment may be carried out after the calender processing, if necessary. The water-repelling treatment may be carried out according to impregnation process, patting process, coating process, etc., using an aqueous dispersion of e.g. fluorine repellant, silicone repellant, etc., followed by drying and that treatment to thereby obtain a water-repellent effect.

The present invention will be described in more detail by way of Examples, but it should not be construed to be limited thereto.

EXAMPLE 1

The process of the invention as illustrated in this Example may be followed by viewing the accompanying drawing.

As the resin used in this Example, the following resin was produced and used as a sample for the subsequent tests:

Distilled water (150 parts by weight), potassium persulfate (0.5 part by weight), sodium dodecylbenzene sulfonate (1.0 part by weight) and acrylamide (3 parts by weight) were fed in a flask, followed by raising the temperature up to 70° C. under $N_2$ puring, thereafter continuously dropwise adding butyl acrylate (66 parts by weight), acrylonitrile (23 parts by weight), acrylic acid (4 parts by weight) and hydroxyethyl methacrylate (4 parts by weight) to complete polymerization and thereby obtain an acrylic emulsion having a solids content of 40%.

A mixture consisting of the above-mentioned acrylic emulsion of butyl acrylate, etc. (solids content: 40%) (250 parts by weight), FLO-THENE(tradename of product made by Seitetsu Kagaku Company: average particle diameter, 25 μm) as a polyethylene filler (10 parts by weight) and a defoamer (1.0 part by weight) was dispersed by means of a disperser, followed by thickening the dispersion with aqueous ammonia up to 5,000 cp (BM type viscometer, 60 rpm), applying the resulting material onto a silicone-treated release paper 1 (see the drawing) by means of Comma Bar Coater 2 (see the drawing) (tradename of an instrument made by Hirano Kinzoku Company) so as to give a dry film thickness of 15 μm, and drying the resulting material at 120° C. for 4 minutes by passage through dryer 3. The film containing the polyethylene filler was twice subjected, by means of Mini Calender Roll 4 (tradename of a roll made by Yuri Roll Machine Company), to calender processing (temperature: 20° C.; linear pressure: 20 kg/cm, and velocity: 10 m/min.) and stripping off the release paper 1 to obtain a porous waterproof film 5.

EXAMPLE 2

As a resin used in the present invention, the following resin was produced and used as a sample for the subsequent tests:

Distilled water (100 parts by weight), potassium persulfate (0.8 part by weight), sodium dodecylsulfate (1.5 part by weight) and itaconic acid (1.0 part by weight) were fed in an autoclave, followed by raising the temperature up to 60° C. under $N_2$ purge, thereafter continuously dropwise adding styrene (47 parts by weight), butadiene (50 parts by weight) and hydroxyethyl acrylate (2 parts by weight) to complete polymerization, neutralizing the resulting SBR latex with aqueous ammonia and further deodorizing it by steam stripping to obtain a SBR latex having a solids content of 50%.

A polyacrylic acid thickening agent was added to a mixture of the above SBR latex (solids content: 50%) (200 parts by weight) with a fluorine resin filler (average particle diameter: 15 μm) (10 parts by weight), followed by thickening the mixture into 3,000 cp (BM type viscometer, 60 rpm) with aqueous ammonia, coating and drying the resulting material, twice carrying out calender processing and stripping a release paper in the same manner as in Example 1 to obtain a porous waterproof, film.

EXAMPLE 3

As a resin used in this Example, the following resin was produced:

Polycaprolactone (number average molecular weight: 1,000) (158 parts by weight), dicyclohexylmethane diisocyanate (109 parts by weight), dimethylol propionate (21 parts by weight) and N-methyl-2-pyrrolidone (240 parts by weight) were fed into a flask, followed by carrying out reaction at 80° to 100° C. in $N_2$ atmosphere to obtain an urethane prepolymer having a NCO content of 3.0%, cooling it, adding triethylamine (16 parts by weight) isophorone diamine (16 parts by weight) and distilled water (444 parts by weight) to obtain an aqueous urethane dispersion having a solids content of 30%, subjecting a mixture of the above aqueous urethane dispersion (333 parts by weight) with a fluorine resin filler (average particle diameter: 15 μm) (10 parts by weight) to coating, drying and twice calender processings and stripping a release paper in the same manner as in Examples 1 and 2 to obtain a porous waterproof film.

COMPARATIVE EXAMPLE 1

For comparison with the present invention, Example 1 was repeated except that no polyethylene filler was used, followed by coating and calender processing in the same manner as in Example 1 to obtain a film containing no polyethylene filler.

COMPARATIVE EXAMPLES 2 AND 3

For comparison with the present invention, materials having removed the fluorine resin filler from the mixtures of Examples 2 and 3 were processed in the same manner as in Examples 2 and 3 to obtain films containing no fluorine resin filler.

The properties of these products are shown in Table 1.

TABLE 1

| | Thermoplastic resin | Organic filler | Thermoplastic resin/organic filler | Gas-permeability sec/100 cc | Water-resistant pressure mmH$_2$O |
| --- | --- | --- | --- | --- | --- |
| Example 1 | Acrylic emulsion | Polyethylene | 100/10 | 400 | 950 |
| Example 2 | SBR latex | Fluorine resin | 100/10 | 320 | 1100 |
| Example 3 | Urethane dispersion | Fluorine resin | 100/10 | 630 | 1300 |
| Compar. ex. 1 | Acrylic emulsion | — | 100/0 | 5000 or more | 1000 |
| Compar. ex. 2 | SBR latex | — | 100/0 | 5000 or more | 1400 |
| Compar. ex. 3 | Urethane dispersion | — | 100/0 | 5000 or more | 1400 |

(Note 1) Gas-permeability: according to JIS L-1096, GURLEY's method.
(Note 2) Water-resistant pressure: according to JIS L-1092, water-resistant pressure tester.
(Note 3) The ratio of thermoplastic resin/organic filler is expressed in terms of weight ratio calculated from solids content.

EXAMPLES 4 TO 8

An acrylic emulsion of butyl acrylate, etc. having a solids content of 40% as in the case of Example 1 was used as a thermoplastic resin and materials obtained by thickening mixtures thereof with a filler having varied its kind and quantity into 5,000 cp (BM type viscometer, 60 rpm) with aqueous ammonia were coated onto a silicone-treated release paper by means of Comma Bar Coater (tradename of a coater made by Hirano Kinzoku Company) so as to give a dry film thickness of 15 μm, followed by drying the resulting material at 100° C., curving it at 130° C. for 2 minutes, placing a nylon taffeta (112 warp yarns/inch and 97 weft yarns/inch) on the release paper coated with the thermoplastic resin containing the filler, subjecting the resulting material to applying and calender processing (temperature 20° C.; linear pressure 20 kg/cm; and velocity 10 m/min.) by means of Mini Calender Roll (trademark of a roll made by Yuri Roll Machine Company) and then stripping the release paper to obtain porous waterproof films.

COMPARATIVE EXAMPLE 4

For comparison with the present invention, processing was carried out in the same manner as in Example 4 except that the filler in Example 4 was not used to obtain a film containing no filler.

These results are shown in Table 2.

resin filler was varied to 100/60 (Comparative examples 5 and 6).

TABLE 3

|  | Filler kind | Particle diameter (μm) | SBR/ organic filler | Calender processing | Gas-permeability (sec/100 cc) | Water-resistant pressure (mmH$_2$O) |
| --- | --- | --- | --- | --- | --- | --- |
| Example 9 | Polyethylene | 15 | 100/5 | Twice | 1070 | 1100 |
| Example 10 | Polyethylene | 15 | 100/30 | Twice | 350 | 700 |
| Example 11 | Fluorine resin | 25 | 100/5 | Twice | 660 | 1000 |
| Example 12 | Fluorine resin | 25 | 100/30 | Twice | 200 | 850 |
| Compar. ex. 4 | None | — | 100/0 | Twice | 5000 or more | 1300 |
| Compar. ex. 5 | Polyethylene | 15 | 100/60 | Twice | 140 | 200 |
| Compar. ex. 6 | Fluorine resin | 25 | 100/60 | Twice | 110 | 250 |

*The ratio of SBR to organic filler is expressed in terms of the ratio of solids contents.

EXAMPLES 13 to 17

Examples 16 and 17 are not examples of the invention but is for purposes of comparison.

The acrylic emulsion of butyl acrylate, etc. (solids content: 40%) used in Example 1 was used as a thermoplastic resin and polyethylene or a silicone resin, each having the average particle diameter varied, was used as a filler, and applying and processing were carried out in the same manner as in Examples 4–8, but varying the thickness of coating to obtain porous waterproof films. These results are shown in Table 4.

In addition, the ratio of the acrylic emulsion to the organic filler was set to 100/15.

TABLE 2

|  | Example 4 | Example 5 | Example 6 | Example 7 | Example 8 | Compar. ex. 4 |
| --- | --- | --- | --- | --- | --- | --- |
| Organic filler, Kind | Polyethylene | Fluorine resin | Urea resin | Silicone resin | Polyester resin | None |
| Average particle diameter (μm) | 15 | 25 | 10 | 20 | 25 | — |
| Acrylic emulsion/ organic filler | 100/15 | 100/15 | 100/20 | 100/15 | 100/20 | — |
| Calender processing | Twice | Twice | Three times | Twice | Three times | Twice |
| Gas-permeability (sec/100 cc) | 470 | 290 | 1030 | 350 | 1330 | 5000 or more |
| Water-resistant pressure (mmH$_2$O) | 800 | 950 | 650 | 900 | 700 | 1300 |

*The ratio of acrylic emulsion to organic filler is expressed in terms of the ratio of the solids contents.

TABLE 4

|  | Filler | Particle size (μm) | Dry film thickness (μm) | Frequency of calendering | Gas-permeability (sec/100 cc) | Water-resistant pressure (mmH$_2$O) |
| --- | --- | --- | --- | --- | --- | --- |
| Example 13 | Polyethylene | 3 | 15 | Twice | 1200 | 1250 |
| Example 14 | Polyethylene | 40 | 20 | Twice | 420 | 600 |
| Example 15 | Silicone resin | 35 | 20 | Twice | 510 | 700 |
| Example 16 | Polyethylene | 0.5 | 15 | Twice | 4450 | 1300 |
| Example 17 | Polyethylene | 60 | 30 | Twice | 270 | 500 |

EXAMPLES 9 to 12

The SBR latex having a solids content of 50% used in Example 2 was used as a thermoplastic resin and polyethylene or fluorine resin, each having the content varied was used as a filler and further, applying and processing were carried out in the same manner as in Examples 4 to 8 to obtain porous waterproof films.

These results are shown in Table 3.

In addition, for comparison with the present invention, the ratio of SBR latex to polyethylene or fluorine

EXAMPLE 18

Example 4 was repeated except that the nylon taffeta was replaced by a sized paper obtained by subjecting a paper of 100% pulp to post-processing with a wax sizing agent and having a basis weight of 25 g/m$^2$ to obtain a composite porous waterproof film.

EXAMPLE 19

The acrylic emulsion of butylacrylate, etc. containing polyethylene filler, used in Example 4 was directly coated onto a nylon taffeta so as to give a dry film thickness of 15μ by means of a roll over knife water, followed by processing the resulting material under the same drying condition and calender conditions as in Example 4 to obtain a porous waterproof film.

COMPARATIVE EXAMPLE 7

For comparison with the present invention, a thermoplastic resin film in advance of being applied onto the nylon taffeta obtained in Example 4 and not subjected to calender processing was stripped from a release paper, followed by applying the film onto the nylon taffeta and measuring its gas-permability and water-resistant pressure.

These results are shown in Table 5.

TABLE 5

| | Base | Coating process | Times of calenderings | Gas-permeability | Water-resistant pressure |
|---|---|---|---|---|---|
| Example 18 | Sized paper | Transfer coating | Twice | 980 | 1100 |
| Example 19 | Nylon taffeta | Direct coating | Twice | 410 | 700 |
| Compar. ex. 7 | Nylon taffeta | Transfer coating | None | 5000 or more | 1400 |

The porous waterproof film provided according to the present invention is usable as it is, or in the form of a composite film obtained by combining the above film with another base having intrinsically gas-permeability such as clothes, paper or the like, for use applications such as garments, waterproofing cover, physiologic goods such as paper diaper, rain coat, etc. and also suitable for disposable use applications.

What is claimed is:

1. A process for producing a gas-permeable waterproof film, which process comprises subjecting a thermoplastic resin composition film consisting essentially of 100 parts by weight of fine particles of an organic thermoplastic resin and 1 to 50 parts by weight of a resin filler selected from the group consisting of thermoplastic and thermosetting resins; said particles having a diameter of 1 to 50μ to calender processing, which consists essentially of
   (a) applying to a release paper or film a liquid dispersion of the filler containing resin;
   (b) drying the dispersion to form a film thereof;
   (c) calendering the film on the release paper or film; and
   (d) separating the film from the release paper or film whereby a gas-permeable, waterproof film is obtained.

2. A process according to claim 1 wherein said calender processing is carried out under conditions of a linear pressure of 1 to 200 kg/cm and a temperature of 0° to 150° C.

* * * * *